United States Patent [19]
Messina

[11] Patent Number: 5,357,945
[45] Date of Patent: Oct. 25, 1994

[54] MULTIPOSITIONAL NEBULIZER DEVICE

[76] Inventor: Robin L. Messina, R.D. #2, Box 353 M, Port Murray, N.J. 07865

[21] Appl. No.: 32,310

[22] Filed: Mar. 17, 1993

[51] Int. Cl.⁵ .................. A61M 11/00; A61M 15/00; A61M 16/10; A62B 18/02
[52] U.S. Cl. .................... 128/200.14; 128/203.12; 128/203.29; 128/205.25; 128/207.14; 128/911; 128/912
[58] Field of Search ............ 128/912, 200.21, 203.12, 128/205.18, 205.25, 204.18, 203.29, 207.14, DIG. 26, 911, 200.14

[56] References Cited

U.S. PATENT DOCUMENTS

| | | | |
|---|---|---|---|
| 3,221,733 | 12/1966 | Beasley | 128/200.14 |
| 3,894,537 | 7/1975 | Camp | 128/200.14 |
| 4,200,093 | 4/1980 | Camp | 128/200.14 |
| 4,253,468 | 3/1981 | Lehmbeck | 128/200.21 |
| 4,257,415 | 3/1981 | Rubin | 128/200.21 |
| 4,327,718 | 5/1982 | Cronenberg | 128/205.12 |
| 4,401,241 | 8/1983 | Cruz | 128/200.21 |
| 4,593,690 | 6/1986 | Sheridan et al. | 128/912 |
| 4,823,784 | 4/1989 | Bordoni et al. | 128/200.21 |
| 4,886,055 | 12/1989 | Hoppough | 128/200.14 |
| 4,949,715 | 8/1990 | Brugger | 128/200.14 |
| 5,027,809 | 7/1991 | Robinson | 128/200.14 |

Primary Examiner—Kimberly L. Asher

[57] ABSTRACT

The present invention is directed to an improved nebulizer attachment for use with a powered nebulizer machine for converting liquid medication into aerosol. It includes a reservoir chamber for liquid medication which is adapted to be oriented substantially vertically, has a gas inlet located thereon for connection to a nebulizer machine and has the capability therein to intermix the incoming gas with the liquid medication to create an aerosol. There is also an aerosol outlet for connection to a face attachment for delivery of the aerosol to a user. The present invention also includes a face attachment indirectly connected to the reservoir chamber. Finally, there is a hollow fitting located between the reservoir chamber and the face attachment. This hollow fitting is formed of a plastic tube having a plurality of circumferential, unconnected corrugations of a semi-flexible nature and has only three rest positions for each such corrugation. One rest position is fully compressed, a second rest position is fully open, and a third rest position is tilted with full compression at one point and fully open at an opposite point to create a single non-180° angle.

6 Claims, 3 Drawing Sheets

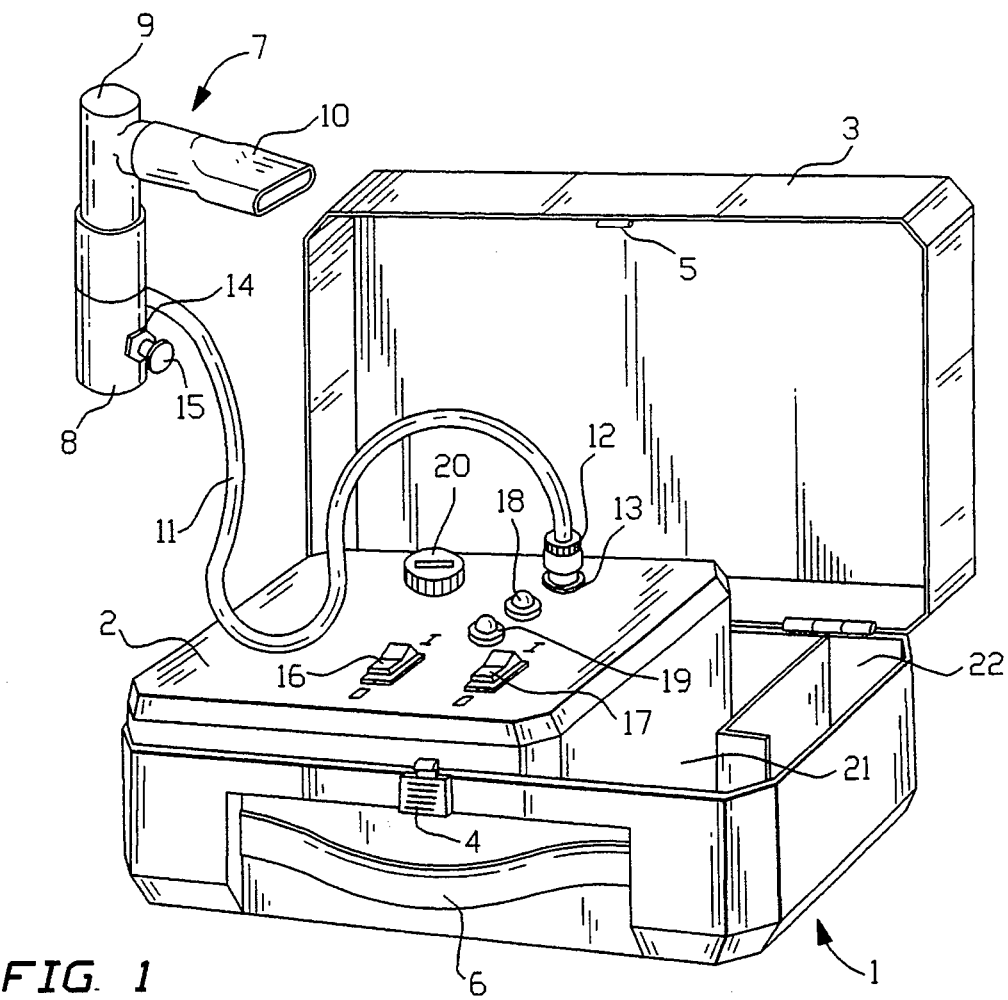
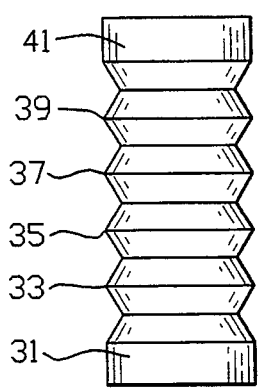
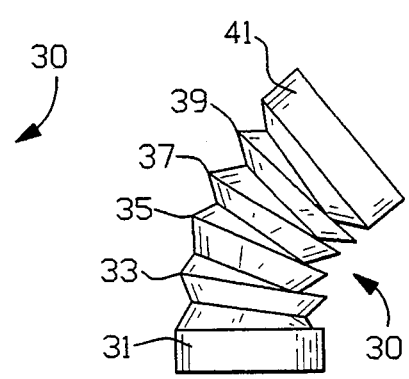
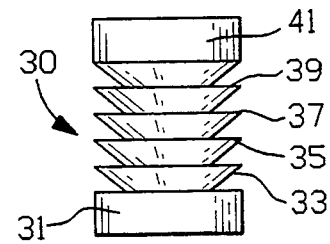
FIG. 1 (PRIOR ART)
FIG. 2
FIG. 3
FIG. 4

MULTIPOSITIONAL NEBULIZER DEVICE

BACKGROUND OF THE INVENTION

1. Field of the Invention

The present invention is directed to a nebulizer for converting liquid medication into aerosol, and, more specifically, to an improved nebulizer attachment. The present invention nebulizer attachment enables a user to set a predetermined, preselected angle other than a straight or right angle of orientation between a nebulizer face attachment and a nebulizer reservoir chamber which must be maintained in a substantially vertical position.

2. Information Disclosure Statement

Nebulizers have been available for a number of years and typically take the form of either stationary devices, meaning permanently affixed devices which are far too heavy to be deemed portable, or portable devices. In either case, the basic components of a nebulizer unit include a nebulizer machine, sometimes referred to as a compressor or pump, a medication reservoir and a face attachment. Hosing is also included to connect the compressor with the reservoir chamber to deliver air or oxygen so as to intermix with the liquid medication to form an aerosol, mist, or gas. The reservoir chamber is then typically attached to a face attachment such as a mask or mouthpiece.

U.S. Pat. No. 3,221,733 issued to Noel F. Beasley in 1965 describes a nebulizer unit, referred to as a pressure breathing therapy unit, which includes a compressor, connecting hose, a medication chamber for the liquid medication, and a face piece, with interconnecting flexible hosing. This invention requires a support arm which is rigid and generally affixes the position of the reservoir chamber and hence the location of the device for a user.

U.S. Pat. No. 3,894,537, issued to Nat Camp in 1975 describes a steam nebulizer which includes an open housing seated atop a steam generator with a nozzle which penetrates into the housing on one side of a baffle and intercepts the steam issuing from a lateral nozzle orifice. The device is attached to a face mask via a flexible hose.

U.S. Pat. No. 4,200,093, issued to Nat Camp in 1980 likewise describes a steam-air inhalator which includes connection via flexible hosing to a face mask, or, alternatively, to a mouthpiece.

U.S. Pat. No. 4,253,468 describes an alternative nebulizer attachment device which includes a liquid medication reservoir chamber, a T-connector, a conduit with a rotor and the ability to attach to a face attachment. Note here that the reservoir and the T-connector which may act as a mouthpiece are at fixed right angles to one another.

U.S. Pat. No. 4,401,241, issued to Exequiel D. Cruz in 1983 describes a nebulizer bottle which includes a flexible neck with a mouthpiece which is typically oriented in the vertical position and which is rotated downwardly and oriented in the horizontal position for use but, due to the springiness or return of the flexible hose portion, this must be uncharged by means of an arrow clip or other attachment means which is inserted into an open loop for fixed orientation in the horizontal position.

U.S. Pat. No. 4,886,055 issued to John M. Hoppough in 1989 describes a nebulizer device which includes an atmosphere adjusting collar both slidably and rotatably mounted on the housing so as to adjust restriction of atmosphere inlet ports on the housing. This is included in the path from the liquid medication reservoir chamber to a face mask and a flexible hosing is included.

U.S. Pat. No. 4,949,715, issued to Stephan Brugger on Aug. 21, 1990 describes a transportable inhalation device which is typical of current day nebulizers. This device includes a portable compressor, connecting hose, reservoir chamber and face attachment, which, in this case, is a mouthpiece. Here, the reservoir chamber must be maintained in a substantially vertical orientation to assure proper nebulization, e.g., atomization or aerosol formation, of the medication, yet the mouthpiece is fixedly attached thereto at a right angle without any capability of changing or adjusting the angle between the mouthpiece and the chamber reservoir.

U.S. Pat. No. 5,027,809, issued to Pat Robinson on Jul. 2, 1991 describes attachments for a hand held aerosol generating nebulizer which enables the patient to adjust exhalation holes to control the ranges of passive to active exhalation resistance, thereby adjusting the expiratory pressure and expiratory respiration. Thus, flexible hoses are used which have one or more ports located therein and which may be stretched open or forced closed depending upon the flexed orientation of the hosing by the user.

Notwithstanding the formidable prior art, it should be noted that none of the prior art references teach, suggest or render obvious the concept of the present invention wherein a semi-flexible hose is used between the face attachment and the reservoir chamber so that only a series of predetermined and preset angles can be achieved in a fixed fashion so that a user can reorient the angle between the face attachment and the chamber. In other words, the present invention specifically enables a user to have a position other than a substantially vertical neck and head position and yet to have the face attachment comfortably fitted to the head at such a different angle while still maintaining the nebulizer reservoir chamber at a substantially vertical orientation.

SUMMARY OF THE INVENTION

The present invention is directed to an improved nebulizer attachment for use with a powered nebulizer machine for converting liquid medication into aerosol. It includes a reservoir chamber for liquid medication which has sides, a base and a top. This chamber is adapted to be oriented substantially vertically and has a structure for holding the liquid medication, has a gas inlet located thereon for connection to a nebulizer machine and has the capability therein to intermix the incoming gas with the liquid medication to create an aerosol. There is also an aerosol outlet for connection to a face attachment for delivery of the aerosol to a user. The present invention also includes a face attachment indirectly connected to the reservoir chamber. Finally, there is a hollow fitting located between the reservoir chamber and the face attachment. This hollow fitting is formed of a plastic tube having a plurality of circumferential, unconnected corrugations of a semi-flexible nature and has only three rest positions for each such corrugation. One rest position is fully compressed, a second rest position is fully open, and a third rest position is tilted with full compression at one point and fully open at an opposite point to create a single non-180° angle. The hollow fitting enables the user to change the angle formed between the reservoir chamber and the face attachment to a fixed single angle selected from a predetermined series of angles, each angle being larger by an increasing number of compressions of the corrugations. Such angles being used incrementally sequential. In preferred embodiments, there is also a T-connector located between the reservoir chamber and the face attachment, and the hollow fitting is located either between the reservoir chamber and the base of the T-connector or the T-connector and the face attachment.

BRIEF DESCRIPTION OF THE DRAWINGS

The present invention will be more fully understood when the specification herein is taken in conjunction with the drawings appended hereto, wherein:

FIG. 1 shows a front oblique view of a prior art nebulizer device;

FIGS. 2,3 and 4 show front views, respectively, of a present invention hollow fitting in its fully opened position, its tilted position and its fully compressed position for use in a nebulizer attachment of the present invention;

DETAILED DESCRIPTION OF THE PRESENT INVENTION

Figure 5:
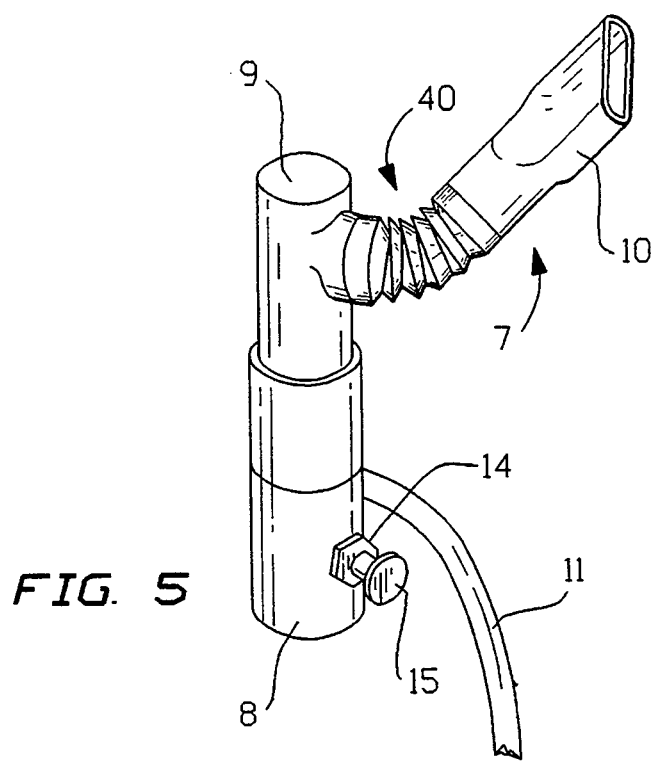
FIG. 5 shows a front oblique view of present invention nebulizer attachment which includes a mouthpiece.
Figure 6:
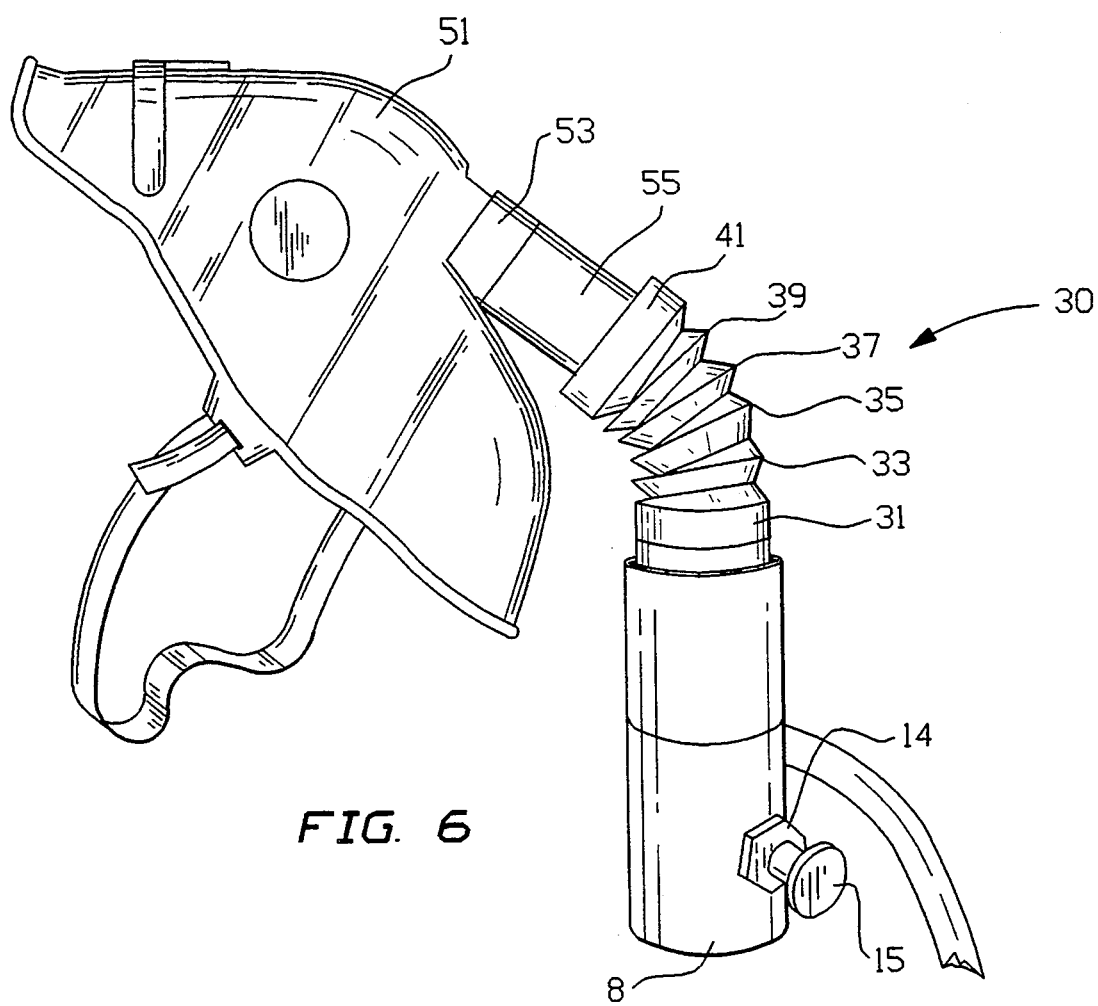
FIG. 6 shows a front oblique view of a present invention nebulizer attachment which includes a face mask; and, FIG. 7 shows a present invention nebulizer attachment which includes a T-connector and shows alternative locations for the hollow fitting used in the present invention.
Figure 7:
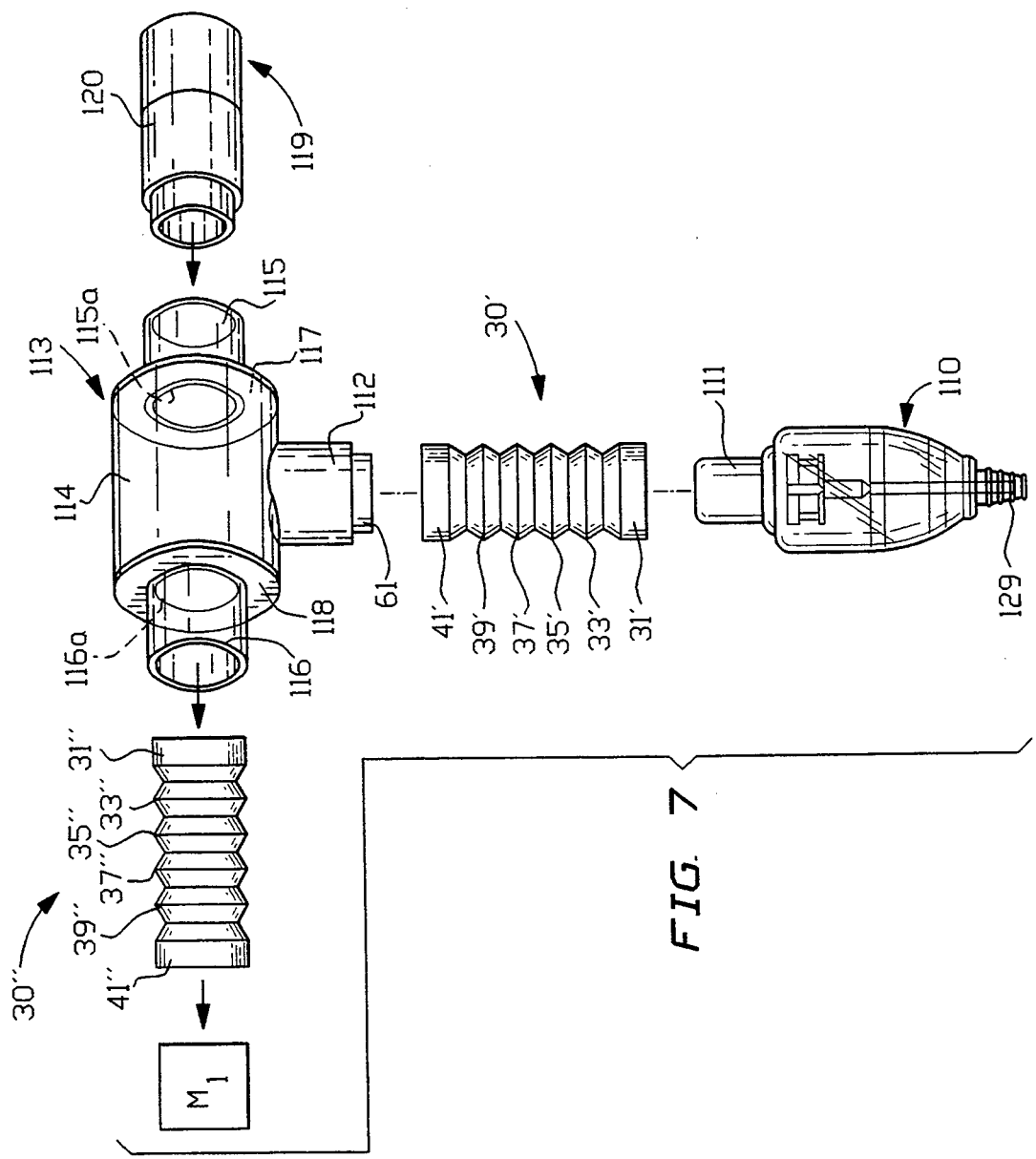

The present invention is directed to a significant problem for asthmatics and other patients who require inhalation medication through a nebulizer. Prior art devices typically involve either a rigid or fixed angle between the nebulizer reservoir chamber and the face attachment or provide for a totally flexible hosing. In the case of the fixed angle devices, a user must maintain his or her head in a substantially vertical position in order to orient the reservoir chamber in a substantially vertical position or must have an awkward and improper angle between the head and the face attachment. In the case of those prior art devices using flexible hosing, the chamber must be held by one hand, lest the slightest movement will cause multiplied swinging of the reservoir chamber and cause a possible misfunction of the nebulizer itself.

Thus, it is an object of the present invention to provide a nebulizer attachment which includes a face attachment and a reservoir chamber with a connecting hollow fitting which will enable the user to adjust the angle between these two components to a predetermined angle selected from a series of angles resulting from the particular design of the hollow fitting, which is described with more detail below.

It is also an object of the present invention to provide a nebulizer user with a nebulizer attachment which enables the user to sit down and lie back, to some extent, or fully, without effecting the required substantially vertical orientation of the reservoir chamber. Thus, by use of the present invention, a user may lie down, sit back in a chair and watch television, lie partially down in a recliner chair or otherwise and set the proper angle between the face attachment and the reservoir chamber to maintain the head position as desired and maintain the chamber as required.

It is further an object of the present invention to provide a nebulizer user with a nebulizer attachment which will enable the user to lean over such as in the case of reading or working at a table or writing or otherwise bending forward and downward.

Referring now to FIG. 1, there is shown a current day prior art nebulizer unit which includes a housing 1 made of plastic, in which all of the electrical components and the compressor or pump are contained. On its upper side, there is a level cover plate 2 and on the back side there is a snap cover 3 which has hinges and a snap lock 4 which interacts with a small projection 5 for closure. A handle 6 is also included on the housing 1. The inhalation device includes an aerosol mister 7 which the patient holds in his or her hand. The mister comprises a lower part which is a reservoir chamber 8 which contains the medication solution to be misted and an upper part 9, as well as a face attachment, in this case, a mouthpiece 10. Compressed air hose 11 serves to supply compressed air into the cavity of the aerosol mister 7. The free end of the compressor air hose 11 terminates in a coupling 12 which is inserted into a receptacle 13 mounted on cover plate 2 on housing 1. Furthermore, a valve 14 which blocks the supply of compressed air into the cavity of the aerosol mister 7 is located in the reservoir chamber 8 of aerosol mister 7. When the push button 15, which is under pretension from a spring is pressed, the valve 14 opens and when the button 15 is released the valve 14 automatically closes. A power switch 16, a switch 17 and an accumulator status light 18 and a recharger status light 19 are mounted on the coverplate 2 of the housing 1. The screw lock of a replaceable air filter is designated with the number 20. A compartment 21 is opened towards the top and serves to receive the aerosol mister 7 during transport of the inhalation device. A compartment 22 is also provided for other accessories. Note here that the angle between the reservoir 8 and the mouthpiece 10 is 90° and fixed. This creates the difficulties described above.

Referring now to FIGS. 2, 3 and 4, there is shown a front view of a fully expanded, tilted and fully compressed hollow fitting 30. As shown in FIG. 2, hollow fitting 30 is fully open and includes end pieces 31 and 41. There between are corrugations 33, 35, 37 and 39. They are not part of a continuous coil or wire but are, at their widest points, unconnected to one another by any infrastructure. While these corrugations are in the fully opened position, they are symmetrical and in a maximum "stretch" rest position. If ends 31 and 41 were pulled, then they may flex or stretch somewhat, but not significantly. In fact, the position shown in FIG. 2 is relatively rigid and could be relied upon to support various components of a nebulizer, provided that the thickness of the plastic is adequate to do so and actual tests have shown that these do work.

FIG. 3 shows hollow fitting 30 wherein the right side of each of the corrugations have been compressed and the left sides have not been compressed so as to cause a tilt. If only one were compressed, then a smaller angle would be formed, and if only two were compressed, then a next larger angle would be formed, and if three were compressed, the angle would get greater, with the maximum angle being created with all of the corrugations being compressed on one side.

FIG. 4 shows hollow fitting 30 wherein the corrugations are all fully compressed. No angle results other than a straight line, but the length is substantially shortened due to the folds in corrugations under full compression. This rest position, as well as those shown in FIGS. 2 and 3, are positions which will maintain fixed relationships between a nebulizer reservoir chamber and a face attachment and thus, hollow fitting 30 is used accordingly in the nebulizer attachment of the present invention.

In this particular embodiment, since the corrugations are of equal size and angles, when they are sequentially compressed on one side, the angle between the ends of hollow fitting 30 becomes larger sequentially at a fixed multiple of the smallest angle created. On the other hand, if the corrugations were different sizes and/or different angles (created, for example, by the tops or bottoms of each corrugation having varying diameters), then sequential compression of one side of the corrugations would result in increasingly larger angles created but they would not be multiples necessarily of the first angle created. While it would seem illogical to create corrugations of different sizes or different angles, it should be understood that it is intended that such variations be covered by the present invention, although the discussion will presume corrugations of equal sizes and angles.

FIG. 4 shows the third rest position of hollow fitting 30 with all of the corrugations fully compressed, as shown. This does not change the angle between the ends of hollow fitting 30 but does shorten its length substantially. Thus, the corrugations the hollow fittings of the present invention specifically have only three rested positions and do not freely swing or sway or otherwise flex and hence, are referred to herein as to "semi-flexible". However, unlike flexible hosing, a substantial pressure must be applied to cause the corrugations to flex and this will not create any oscillation or free flexing but will only snap the corrugation into a different rest position if it is not already in the rest position that would be the same as the direction of the force applied to it.

Thus, the present invention includes a nebulizer arrangement or attachment which necessarily contains the hollow fitting described above as a connection, either directly or indirectly, between the nebulizer chamber and the face attachment. However, it should be noted that while the hollow fitting is described herein and is shown as a separate unit, conceivably the face attachment could be a formed extension of the hollow tubing without exceeding the scope of the present invention. In other words, the end 41 of hollow fittings 30 shown in FIG. 2 could be molded and extended to form a mouthpiece or other face attachment and the present invention scope would not be exceeded.

FIG. 5 shows a blown-up portion of the prior art device shown in FIG. 1 with identical parts identically numbered. However, a hollow fitting 40 much like hollow fitting 30 shown in FIG. 2, is attached between the upper part 9 of the hand held nebulizer chamber reservoir 8 and the mouthpiece 10. This enables a user to maintain the reservoir chamber 8 in a vertical position while adjusting mouthpiece 10 to a predetermined angle by compressing one side of one or more corrugations of hollow fitting 40.

FIG. 6 shows an alternative embodiment of the present invention utilizing the chamber 8 of the nebulizer of FIG. 1 but also utilizing the hollow fitting 30 of the present invention shown in FIGS. 2 through 4, with like parts again like numbered. Note that mask 51 has an inlet 53 with an extension 55 connected to the upper end 41 of hollow fitting 30. This enables the user to lie back or lean forward or otherwise have the head with face mask 51 on it in a non-vertical position and to preset a fixed angle between face mask 51 (inlet 53) and nebulizer reservoir chamber 8. Again, the corrugations are compressed as desired to set the angle for the user.

FIG. 7 shows yet another alternative embodiment nebulizer which represents a state-of-the-art device. Herein, there is a nebulizer reservoir chamber 110 of commercially available construction with an aerosol outlet 111 and an air inlet 129. T-connecter 113 has an inlet 112 and a cylindrical aerosol reservoir 114 with an axially aligned inlet opening 115A and an outlet 116 communicating with reservoir 114 at outlet opening 116A. The reservoir 114 has respective end walls 117 and 118, as shown. Mating with inlet 115 is a one-way attachment which comprises conduit sections 119 and 120 and these may be used by the user to hand control additional air mixture to change the flow rate or a baffle could be included in cylinder 119 which could be adjustable. In any event, various other devices may be attached to T-connector 113 without affecting the present invention. Here, hollow fitting 30' which is located between aerosol outlet 111 and connector 61 at T-connector inlet 112. This would enable the user to fixedly adjust the angle between T-connector 113 and reservoir chamber 110. Outlet 116 could be extended to be used as a mouthpiece or could be attached to a mouthpiece (not shown). In the alternative, inlet 112 of T-connector 113 could be connected directly to reservoir chamber 110 and hollow fitting 30'' could be connected at the outlet 116 of T-connector 113 and this could be subsequently connected to a mask, mouthpiece or other face attachment which are commercially available (not shown) in full perspective but simply shown as box $M_1$. $M_1$ could be an extension of hollow fitting 30'' or could be any other attachment which is commercially available.

Obviously, numerous modifications and variations of the present invention are possible in light of the above teachings. It is therefore understood that within the scope of the appended claims, the invention may be practiced otherwise than as specifically described herein.

What is claimed is:

1. An improved nebulizer attachment for use with a powered nebulizer machine for converting liquid medication into aerosol, which comprises:

(a) a reservoir chamber for liquid medication, having sides, a base and a top, said reservoir chamber adapted to be oriented substantially vertically during use and having structure for holding said liquid medication, said reservoir chamber having a gas inlet located thereon for connection to a nebulizer machine, and having means therein to intermix gas and liquid medication to create an aerosol, and having an aerosol outlet for connection to a face attachment for delivery of aerosol to a user;

(b) a face attachment indirectly connected to said reservoir chamber;

(c) means for maintaining said reservoir chamber in a vertical position without restricting the position of the user, said means for maintaining said reservoir chamber in a vertical position comprising a hollow fitting located between said reservoir chamber and said face attachment, said hollow fitting being formed of a plastic tube having a plurality of circumferential, unconnected corrugations of a semi-flexible nature and having only three rest positions for each such corrugation, one being fully compressed, one being fully open and one being tilted with full compression at one point and fully open at an opposite point to create a single non-180 angle, said unconnected corrugations of said hollow fitting comprising means for changing an angle formed between said reservoir chamber and said face attachment from a first selected position to another selected position, said selected positions created by the user selectively changing the rest positions of one or more of said unconnected corrugations.

2. The nebulizer attachment of claim 1, wherein said face attachment is a face mask.

3. The nebulizer attachment of claim 1, wherein said face attachment is a mouthpiece.

4. The nebulizer attachment of claim 1, further comprising a T-connector located between said reservoir chamber and said face attachment, said T-connector having a lower vertical tubular section for connection to said reservoir chamber and an upper horizontal tubular section for connection to said face attachment.

5. The nebulizer attachment of claim 4, wherein said hollow fitting is located between said vertical tubular section and said reservoir chamber.

6. The nebulizer attachment of claim 4, wherein said hollow fitting is located between said horizontal tubular section and said face attachment.

* * * * *